US010112010B2

(12) United States Patent
Miyamoto

(10) Patent No.: US 10,112,010 B2
(45) Date of Patent: Oct. 30, 2018

(54) INFUSION INJECTION SYSTEM

(71) Applicant: I'm Co., Ltd., Fukuoka (JP)

(72) Inventor: Isshin Miyamoto, Fukuoka (JP)

(73) Assignee: I'm Co., Ltd., Fukuoka (JP)

( * ) Notice: Subject to any disclaimer, the term of this patent is extended or adjusted under 35 U.S.C. 154(b) by 0 days.

(21) Appl. No.: 15/573,564

(22) PCT Filed: Oct. 21, 2016

(86) PCT No.: PCT/JP2016/081292
§ 371 (c)(1),
(2) Date: Nov. 13, 2017

(87) PCT Pub. No.: WO2017/069246
PCT Pub. Date: Apr. 27, 2017

(65) Prior Publication Data
US 2018/0099090 A1 Apr. 12, 2018

(30) Foreign Application Priority Data
Oct. 21, 2015 (JP) .................................. 2015-207119

(51) Int. Cl.
*A61M 5/172* (2006.01)
*A61M 5/14* (2006.01)
A61M 5/168 (2006.01)

(52) U.S. Cl.
CPC .......... *A61M 5/172* (2013.01); *A61M 5/1411* (2013.01); *A61M 5/16831* (2013.01); *A61M 5/16804* (2013.01)

(58) Field of Classification Search
CPC ............ A61M 5/1689; A61M 5/16804; A61M 2205/14; A61M 2205/3306; A61M 39/28;
(Continued)

(56) References Cited

U.S. PATENT DOCUMENTS

| 6,491,659 B1 * | 12/2002 | Miyamoto | .......... | A61M 5/1689 |
| | | | | 604/30 |
| 2004/0193453 A1 * | 9/2004 | Butterfield | ............ | A61M 5/172 |
| | | | | 705/2 |

(Continued)

FOREIGN PATENT DOCUMENTS

| JP | 0663135 | 3/1994 |
| JP | 3185064 A2 | 7/2001 |

(Continued)

OTHER PUBLICATIONS

International Search Report dated Jan. 10, 2017 issued in PCT/JP2016/081292.

*Primary Examiner* — Brian Miller
(74) *Attorney, Agent, or Firm* — Rankin, Hill & Clark LLP

(57) ABSTRACT

An infusion injection system wherein, when injecting a drug solution into a patient using an infusion set and an automatic infusion device, the automatic infusion device confirms various pieces of information regarding the infusion set in order to provide safe infusion for the patient, and to allow the user to assess the infusion information and manage a proper disposal procedure, wherein
whether an infusion set is properly mounted is judged and if the judgment is positive, information stored in an IC tag attached to a drip tube 15 is read out by an IC tag reader unit 59 in an automatic infusion device 7, and information matching is verified between the read-out information and the information set beforehand for the automatic infusion device 7, and wherein control operations are performed only when the verification is a match.

5 Claims, 12 Drawing Sheets

(58) Field of Classification Search
CPC ............ A61M 39/281; A61M 5/16813; A61M 5/172; A61M 5/1411; A61M 5/16831; A61M 5/14; A61M 5/168
See application file for complete search history.

(56) References Cited

U.S. PATENT DOCUMENTS

| | | | | |
|---|---|---|---|---|
| 2013/0177455 A1* | 7/2013 | Kamen | ............... | G06F 19/3418 417/313 |
| 2013/0197469 A1* | 8/2013 | Sharvit | ................. | A61M 5/172 604/500 |
| 2014/0316370 A1* | 10/2014 | Mernoe | ................ | A61M 5/1411 604/500 |
| 2014/0318639 A1* | 10/2014 | Peret | ....................... | F16K 31/02 137/386 |
| 2015/0002677 A1* | 1/2015 | Peret | ......................... | G06T 5/50 348/160 |
| 2015/0157791 A1* | 6/2015 | Desch | .................... | G16H 10/65 604/506 |
| 2016/0051750 A1* | 2/2016 | Tsoukalis | .............. | A61M 5/142 604/151 |
| 2018/0099090 A1* | 4/2018 | Miyamoto | ............ | A61M 5/172 |

FOREIGN PATENT DOCUMENTS

| | | | |
|---|---|---|---|
| JP | 200395440 | | 4/2003 |
| JP | 200634845 | | 2/2006 |
| JP | 2007487 | A2 | 1/2007 |
| JP | 4587597 | B2 | 11/2010 |
| JP | 20125756 | | 1/2012 |
| WO | 2013071934 | A1 | 5/2013 |

* cited by examiner

INFUSION INJECTION SYSTEM

TECHNICAL FIELD

The present invention relates to an infusion injection system, and particularly to an infusion injection system employing an infusion set and an automatic infusion device to infuse a drug solution into a patient.

BACKGROUND ART

The inventor of the present application has been developing a technique with respect to an infusion injection system. For example, the present inventor holds a patent disclosed in Japanese Patent No. 4587597 (Patent document 1). Description will be made regarding the points of this technique. This technique relates to an automatic infusion device including a drip tube pressing holder, a flow regulation unit, a drip sensor, a calculation mechanism, an actuator, a liquid level sensor, and a control mechanism. Here, the drip tube pressing holder is provided in order to detachably mount a drip tube provided to an infusion set to be connected to an infusion bottle. The flow regulation unit is arranged below the holder, and is configured to instruct a presser to press and narrow an outlet-side tube of the drip tube so as to enable flow regulation. The drip sensor is configured to detect a liquid drop that drips through the internal space of the drip tube based on received light intensity. The calculation mechanism is configured to calculate the measurement value of the flow based on the number of drops detected by the drip sensor and the measurement time. The actuator is provided to the flow regulation unit, and is configured to move the presser in a front-back direction. The liquid level sensor is arranged at a position below the drip sensor, and is configured to detect the liquid stored in the drip tube based on the received light intensity. At the start of infusion, the control mechanism temporarily instructs the presser to close the tube, following which the control mechanism partly opens the tube. In this stage, when judgment is made that the measurement, value of the flow is equal to or greater than a flow limit value, the control mechanism drives the actuator so as to press and narrow the tube, thereby reducing the flow. This allows the flow of the infusion to be controlled within a predetermined range with a set quantity of flow as its center. Furthermore, the control mechanism is capable of judging the mounting state of the infusion set. With such an arrangement, the control mechanism performs the judgement based on a first output of the drip sensor and a second output of the liquid level sensor. Specifically, when the first output exhibits the same degree of a low-level output value as the second output, when the second output exhibits the same degree of a high-level output value as the first output, or when the second output indicates the output value at the liquid level, judgment is made that the mounting state is abnormal.

At an actual medical treatment site, even if such a technique is employed, there is a need to input accurate information with respect to an infusion set as a condition setting for an automatic infusion device in order to accurately infuse a drug by means of the infusion set and the automatic infusion device. One of the most important pieces of information is the kind of the drip tube (drip amount: drops/ml). Two kinds of drip tubes, i.e., a 20 drops/mi type and a 60 drops/mi type, are required by domestic Japanese law with respect to pharmaceuticals and medical devices. That is to say, two kinds of infusion sets are employed at medical practice sites. One is an infusion set including a drip tube in which the sum total of 20 drops of a drug dripped from a drug outlet of the drip tube is 1 ml. The other is an infusion set including a drip tube in which the sum total of 60 drops of a drug dripped from a drug outlet of the drip tube is 1 ml.

Furthermore, other techniques are known as disclosed in Japanese Patent Application Laid Open No. 2012-5756 (Patent document 2), Japanese Patent Application Laid Open No. 2007-487(Patent document 3), and Japanese Patent Application Laid Open No. 2003-95440(Patent document 4). With the technique disclosed in Patent document 2, a wristband IC tag and a drug prescription IC tag are employed. The wristband IC tag stores at least patient identification information for identifying the patient. The drug prescription IC tag storing information with respect to the patient identification information and at least the drug to be infused into the patient and the amount to be infused are employed. The information stored in the IC tags are read out and is verified. Subsequently, a drug is properly infused into the patient who is to receive the infusion according to the information with respect to the amount of the drug to be infused. With the technique disclosed in Patent document 3, at least two IC tags are provided. One IC tag is attached to an infusion pack at a position such that information cannot be read out unless the infusion is completed, so that the completion of the infusion can be properly asserted. With the Patent document 4, an IC tag is attached to an infusion pack. After the information is read out from the IC tag, this allows a drug company and drug distribution company to acquire information, via a communication line, with respect to the drugs consumed at the medical institution.

In this manner, IC tags are becoming a technology that is employed in the medical field.

Patent Literature

[Patent Document 1]
  Japanese Patent No. 4587597
[Patent Document 2]
  Japanese Patent Application Laid Open No, 2012-5756
[Patent Document 3]
  Japanese Patent Application Laid Open No. 2007-487
[Patent Document 4]
  Japanese Patent Application Laid Open No. 2003-95440

SUMMARY OF INVENTION

Technical Problem

The aforementioned techniques are known. However, the following problems arise at medical treatment sites.

In a case in which a drug is infused with an incorrect drip tube, the following problem occurs. For example, in a case of making a flow setting in which 100 ml of a drug is infused with a flow rate of 100 ml/h, infusion with a 20 drops/mi drip tube provides 20,000 drops per hour in contrast, infusion with a 60 drops/ml drip tube provides 60,000 drops per hour. Accordingly, in a case of making incorrect settings, this leads to an infusion flow that is three times or ⅓ of the target flow rate of the drug. That is to say, such a setting error of the drip tube has the potential to cause a serious medical accident.

Furthermore, an accurate check cannot be made for the information with respect to the executed infusion (target infusion amount, flow rate, infusion start time, infusion end time, number of suspensions of the infusion, time point of every suspension of the infusion, number of times various kinds of alarms such as an abnormal flow rate alarm etc., have been issued, time points at which such alarms have been issued, and the like). Accordingly, it is difficult to develop preventive measures for preventing the recurrence of errors in the infusion. Furthermore, a highly toxic residual liquid remains in an infusion set after an anti-cancer drug has been infused. In actuality, information cannot be obtained with respect to whether or not normal disposal with appropriate treatment has been performed.

Description will be made regarding such proper disposal treatment for the infusion set. In a case in which an anti-cancer drug is infused in chemotherapy, at many medical treatment sites, after the infusion of an anti-cancer drug is performed for a given infusion set, washing of the infusion set (washout) with a physiological saline solution is carried out as a last step as a rule, and the subsequent disposal steps are designed on this basis. The reason for this is that, in a case in which such an anti-cancer drug remains as a residual liquid in a drip tube or tube of an infusion set, such a washout step reduces, as much as possible, the potential for a droplet to fall from as introduction needle and the potential for exposure of an anti-cancer drug to the air. As a result, such as arrangement protects medical staff from such a toxic anti-cancer drug.

Some kinds of anti-cancer drugs can elute a plasticizer (DEHP: endocrine disruptor) from PVC used as a material of a tube of an infusion set. In some cases, an infusion set formed of a PVC-free material is required depending on the kind of as anti-cancer drug. Thus, there is a need to perform anti-cancer drug infusion based on a verification result of matching between the material of the infusion set and the infusion information, but a method for obtaining the verification result of the matching has not been established.

Accordingly, it is a purpose of the present invention to provide an infusion injection system configured such that when injecting a drug solution into a patient using as infusion set and an automatic infusion device, the automatic infusion device confirms various pieces of information regarding the infusion set in order to provide safe infusion for the patient, and to allow the user to assess the infusion information and manage a proper disposal procedure. Furthermore, in particular, it is a purpose of the present invention to provide an infusion injection system that is capable of preventing nurses from making mistakes in important settings of the automatic infusion device, thereby providing accurate infusion. In addition, it is a purpose of the present invention to provide an infusion injection system configured to store the infusion information and to allow the user to check the infusion information in order to protect the medical staff, mainly from a toxic anti-cancer drug in an anti-cancer drug infusion.

Solution of Problem

The first aspect of the present invention relates to an infusion injection system comprising: a drip tube comprising an IC tag having readable information with respect to an infusion set to be connected to an infusion bottle; and an automatic infusion device comprising a main body on which the drip tube is to be mounted. With the infusion injection system, a drug solution stored in the infusion bottle is infused into a patient via the drip tube provided to the infusion set under conditions determined beforehand according to a control operation of the automatic infusion device. The automatic infusion device comprises: a readout mechanism that starts readout of the information with respect to the infusion set held by the IC tag in response to proper mounting of the drip tube on the main body; a storage mechanism that stores information input beforehand, which is to match the information with respect to the infusion set held by the IC tag; an information verification mechanism that verifies information matching between the information read out by the readout mechanism and the information stored in the storage mechanism; and a control mechanism that starts an operation, under the conditions determined beforehand, by the automatic infusion device in response to an operation start signal input by a user when the result of the verification obtained by the information verification mechanism is a match.

The second aspect of the present invention is the infusion injection system of the first aspect, wherein, when the result of the verification obtained by the information verification mechanism is a mismatch, the control mechanism does not start the operation under the conditions determined beforehand by the automatic infusion device.

The third aspect of the present invention is the infusion injection system of the first aspect, wherein, the infusion injection system is configured to allow the user to change the information to be matched which is stored in the storage mechanism once the result of the verification obtained by the information verification mechanism is a match. In a case in which the information to be matched has been changed by the user, the control mechanism starts the operation under the conditions thus changed in response to the operation start signal input by the user, even in a case in which the result of the verification obtained by the information verification mechanism is a mismatch after the change by the user.

The fourth aspect of the present invention is the infusion injection system of the third aspect, wherein, the infusion injection system is configured as a natural-fall infusion injection system. The infusion injection system further comprises a detection mechanism that detects an abnormal state in which the control operation has not been performed under the conditions determined beforehand or otherwise under the conditions thus changed. After the user forcibly suspends the operation or otherwise the operation is automatically suspended according to an abnormal state detected by the detection mechanism, the control circuit disables restarting of the operation even if the operation start signal is input by the user before the user changes the information stored in the storage mechanism after the suspension of the operation.

The fifth aspect of the present invention is the infusion injection system of the third or the fourth aspect, wherein, the storage mechanism records a information change history. As described above, by recording such a history, this allows infusion management to be performed. In addition, the history thus recorded can be effectively used for the future should be noted that the storage mechanism may be configured as a distributed system employing cloud computing.

The sixth aspect of the present invention is the infusion injection system, wherein, the IC tag according to the first aspect is provided to an upper portion of the drip tube. Furthermore, the readout mechanism is arranged such that it faces the IC tag so as to provide the minimum straight-line distance between them. With such an arrangement, the IC tag reader, which is a readout mechanism, is arranged at an optimum position that provides a narrow wireless field. As a result, this allows an IC tag readout operation to be performed in a sure manner. Furthermore, this allows the IC tag to be configured as a very compact IC and to have a short antenna length. This allows the IC tag to be mounted on a narrow space such as the drip tube. Furthermore, the IC tag is provided to such an upper portion of the drip tube. This reduces the potential for a droplet of a drug, water, or the like to fall onto the IC tag. Thus, such an arrangement suppresses a risk of abnormal operations or the like.

The seventh aspect of the present invention is the infusion injection system, wherein, in the automatic infusion device according to the first or the sixth aspects, the main body includes a mechanism configured to hold the drip tube such that it is surrounded on at least two facing sides. Furthermore, the automatic infusion device includes a detection mechanism that detects whether or not the drip tube has been mounted on the main body in a proper state. The readout mechanism is instructed to start a readout operation in response to a detection output of the detection mechanism.

The eighth aspect of the present invention is the infusion injection system, wherein, the automatic infusion device according to any one of the first, sixth, and seventh aspects includes a notifying mechanism that issues a notice when the result of the verification obtained by the information verification mechanism is a mismatch. Examples of methods for issuing a notice include a notice in the form of sound, in addition to an alarm display. As a method for issuing as alarm, various kinds of methods may be employed, examples of which include lighting, blinking, lighting in red or the like that indicates an abnormal state. As described above, in the case in which the result of the verification is a mismatch, a notice thereof is issued. That is to say, an alarm is issued so as to prompt the medical staff to make appropriate settings for the automatic infusion device. This allows the information with respect to the infusion executed with the infusion set to be stored. Furthermore, this allows the information thus stored to be checked and managed. Thus, this allows the medical staff to develop a preventive measure for preventing the recurrence of errors in the infusion. In addition, this allows a check to be made regarding whether or not disposal has been executed normally for an infusion set that was used to infuse a highly-toxic anti-cancer drug.

It should be noted that specific examples of the information pieces stored in the IC tag as the information relating to the infusion set include the date and place of manufacture of the infusion set, the positions and number of side tubes, the material of the infusion set, the kind of bottle needle, and the drip rate of the drip tube (drops/ml). The information may be verified for all the information pieces. Also, a part of the information pieces may be employed for the verification. Also, only a particular information piece may be employed for the verification. In the information verification, in order to reduce the data to be handled, the information pieces may be associated with a serial number. The data readout operation may be performed for such a serial number, and the verification may be performed for the data thus read out.

Also, in the actual infusion operation, the storage mechanism may be configured to store at least one or more information pieces from among the infusion start time and date, the total amount of infusion, the flow rate, the occurrence of abnormal flow, and the time at which abnormal flow has occurred. Also, a transmission mechanism may be configured to transmit, via wireless communication, at least one or more information pieces from among the information with respect to the infusion executed by means of the infusion set, i.e., from among the infusion start time and date, the total amount of infusion, the flow rate, the occurrence of abnormal flow, and the time at which abnormal flow has occurred. This facilitates unified management of the information, which can be used to provide an infusion injection system with further improved safety, and can be used preventing an error that has occurred from occurring in the next infusion and subsequent infusions. Such an arrangement can be effectively employed to prevent the recurrence of infusion accidents.

Also, the first aspect and so forth of the present invention as described above may be embodied as a method, a computer program, a recording medium, or a sub-combination component of the infusion injection system such as an automatic infusion device, a drip tube, and the like.

Advantageous Effects of Invention.

With the present invention, an IC tag is provided to a drip tube having a limited mounting space. A readout mechanism such as an IC tag reader reliably reads out the information with respect to the infusion set, in particular, specification information on the drip tube, stored in the IC tag in response to proper mounting of the drip tube. As a result, this prevents the occurrence of errors the infusion due to inappropriate mounting of the drip tube. Furthermore, information matching is verified between the information thus read out from the IC tag and setting values which are input beforehand to an automatic infusion device and are to be matched with the information with respect to the infusion set held by the IC tag. After the result of the verification is a match, and moreover, after a user such as a nurse or the like performs visual checking of the information, after a double-check is performed, by a machine and by a person, upon pressing a start button or the like, infusion is started for a patient. As a result, this prevents the occurrence of errors in setting the infusion conditions before the actual infusion. In particular, when the result of the verification is a mismatch, the infusion is not started even if the user presses the start button or the like, thereby preventing human error in a sure manner. Additionally, at medical treatment sites, in a case of simply executing a fixed sequence, in some cases, this kind of operation may lead to a problem. In order to solve such a problem, the configuration of the present invention allows the user to change the conditions once confirmation has been made that the result of the verification is a match. This allows judgement to be made regarding whether or not the user is allowed to change the conditions. Furthermore, this supports a flexible response according to the situation of the patient, thereby providing a system having an advantage based on manual operations by a person. In particular, is a case in which the automatic infusion device employs a natural-fall infusion mechanism, abnormal states such as an abnormal drip rate, etc. may readily occur, unlike a system controlled by a pump or the like. Thus, it is notably important to employ such a flexible system from this viewpoint.

BRIEF DESCRIPTION. OF DRAWINGS

Figure 3:
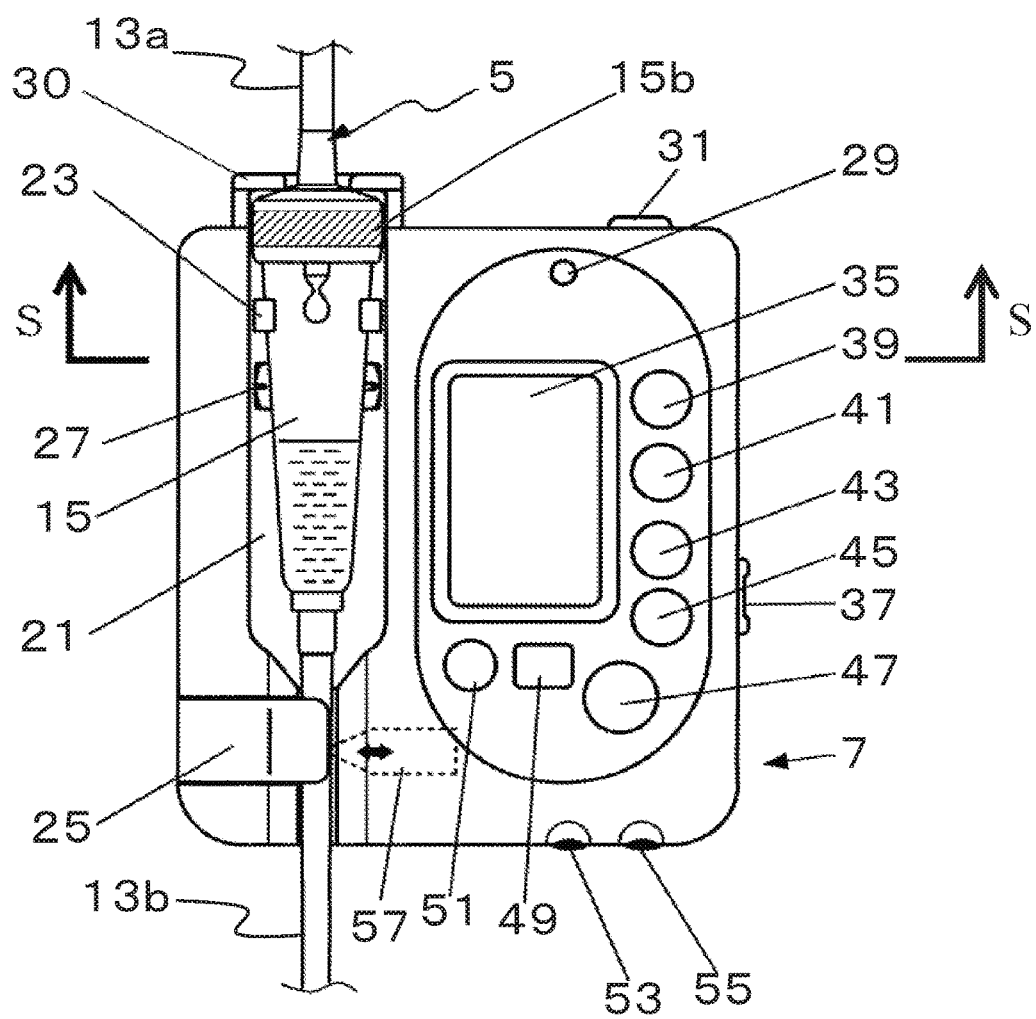
FIG. 3 is a front view showing a state in which a drip tube with an IC tag is provided to the main body of the automatic transfusion apparatus of the transfusion system shown in FIG. 1.
Figure 6A:
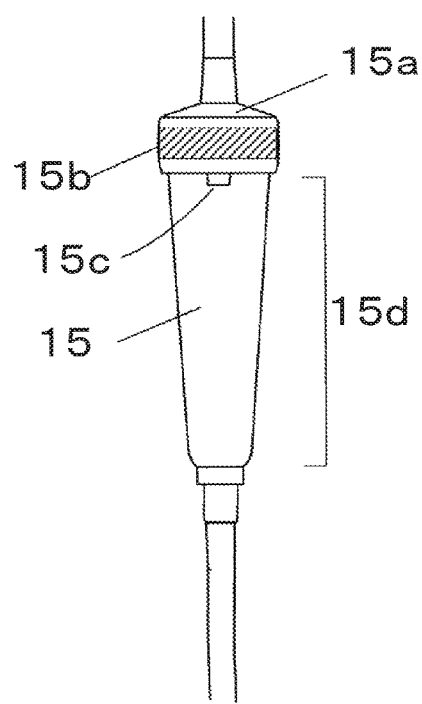
Figure 6B:

FIGS. 6A and 6B are diagrams for describing the IC tag attached to the drip tube shown in FIG. 3, and specifically, FIG. 6A is a front view showing a state in which a sheet-shaped IC tag is fixed by adhesion to a cap portion of the drip tube, and FIG. 6B is a back view showing the sheet-shaped IC tag as viewed from the adhered face thereof, and showing a layout thereof including an antenna and an IC chip.

Figure 1:
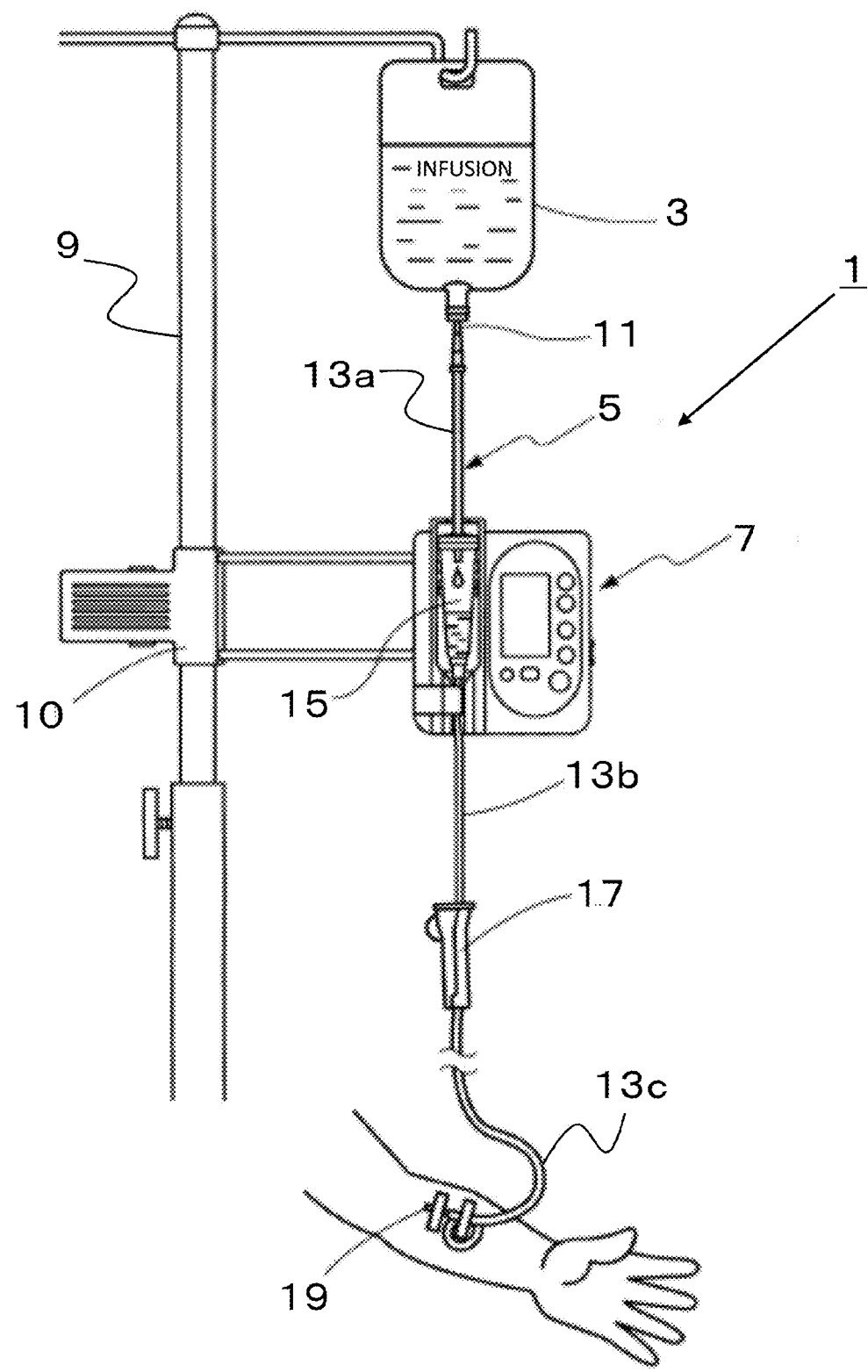
FIG. 1 is an overall view showing a state in which a transfusion system according to an embodiment of the present invention is employed.
Figure 7:
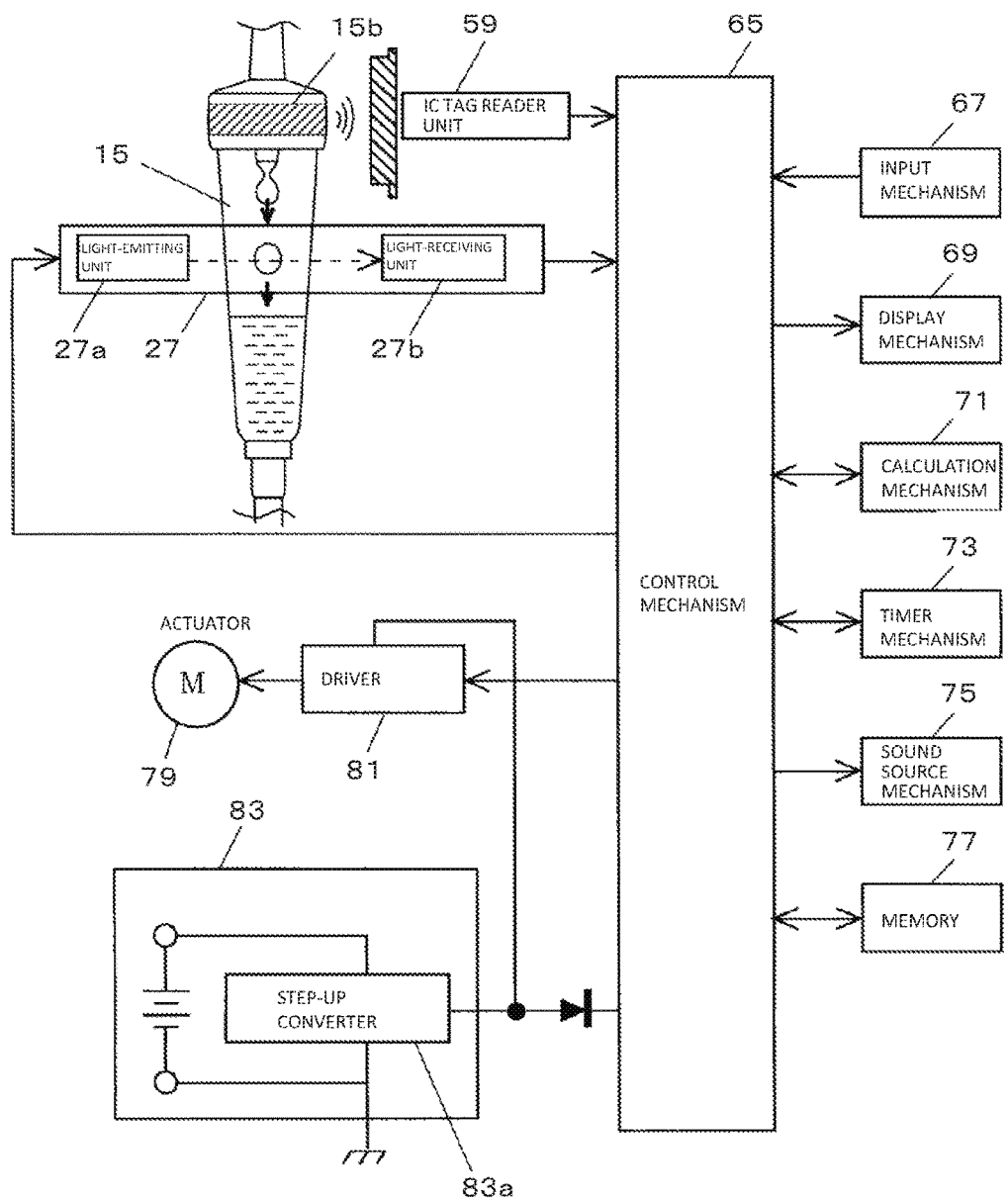

FIG. 7 is a block diagram showing a control circuit of the automatic infusion device of the infusion injection system shown in FIG. 1 and configurations relating to the control circuit.

Figure 8:
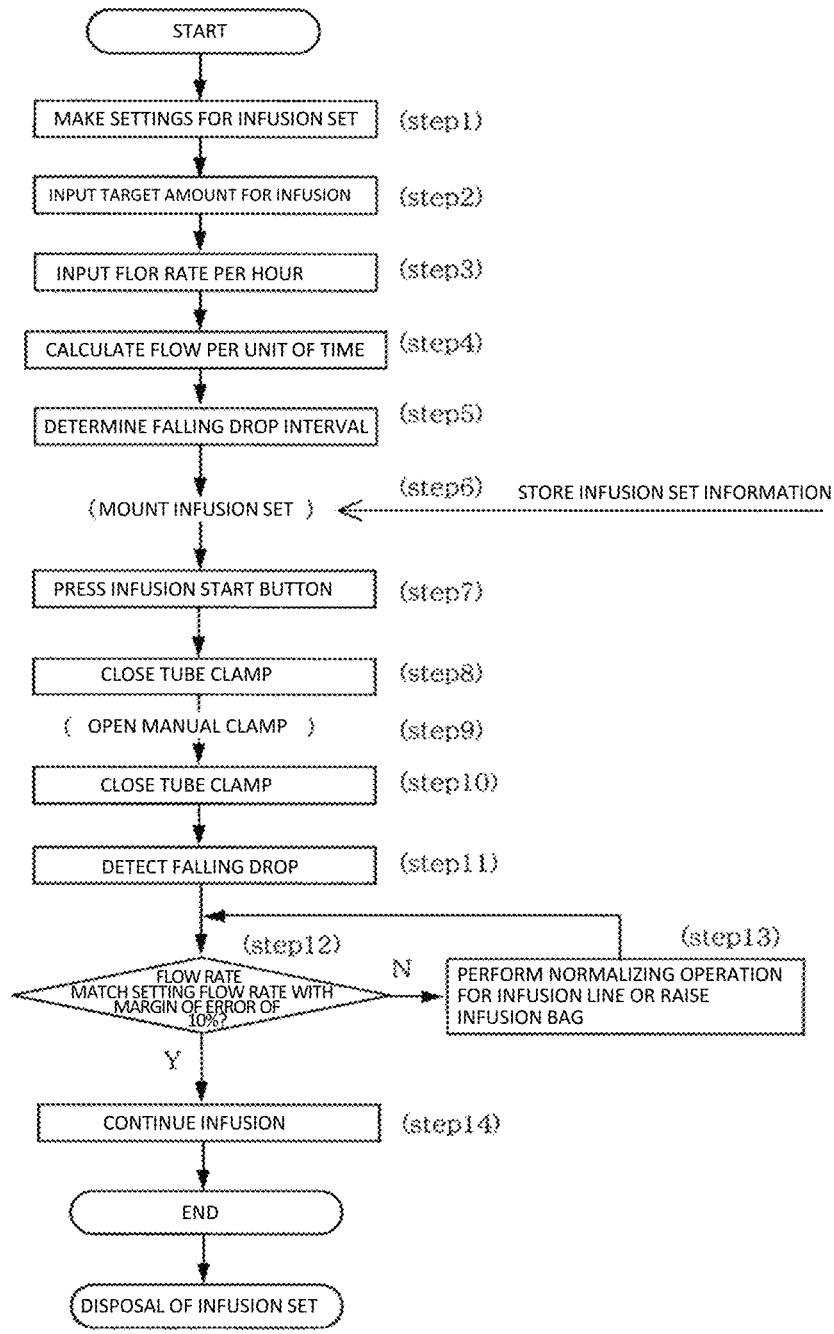

FIG. 8 is a flowchart showing the operation of the automatic transfusion apparatus of the transfusion system shown in FIG. 1.

Figure 9:
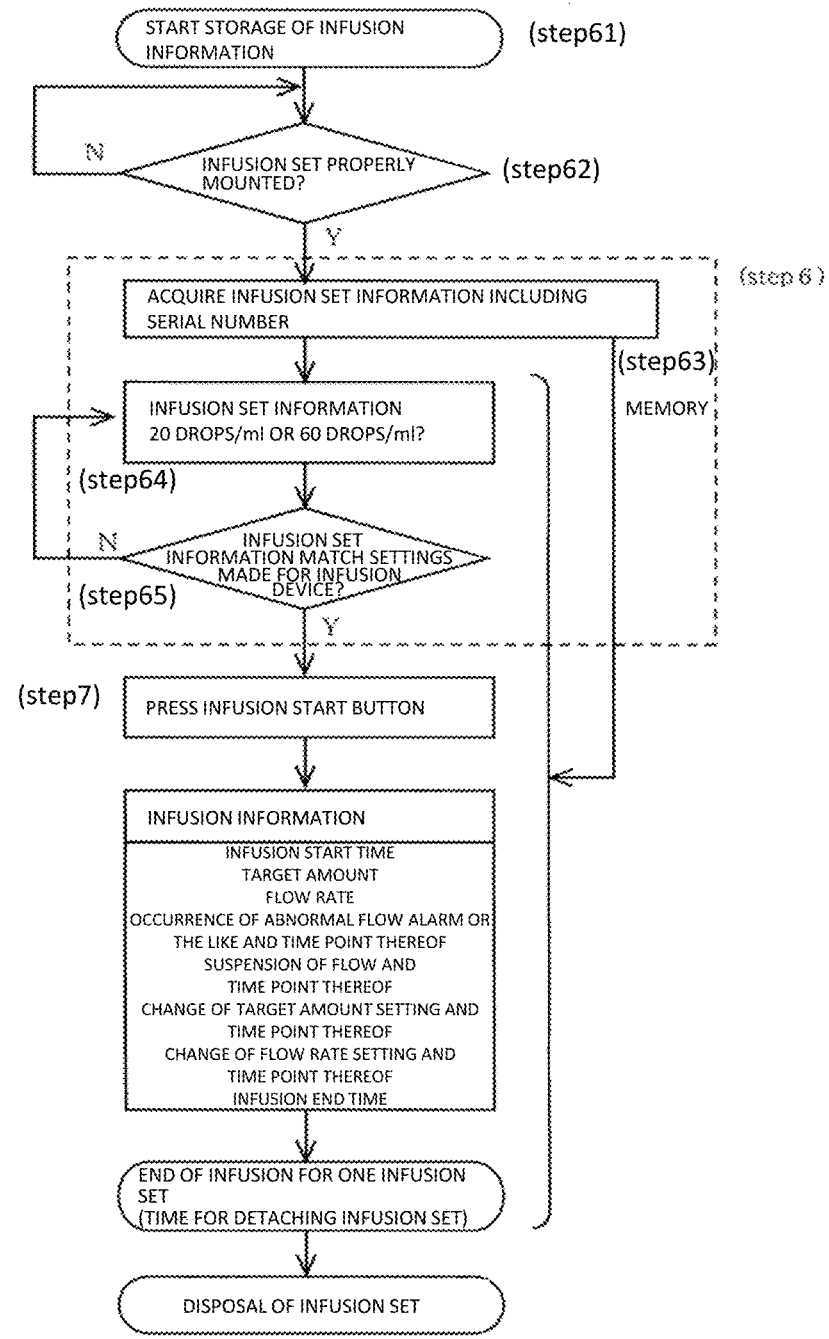

FIG. 9 is a flowchart showing a detailed operation in step 6 shown in FIG. 8, and a procedure performed by means of the automatic infusion device of the infusion injection system show in FIG. 1, which is from the judgment operation regarding whether or not the infusion set has been normally mounted up to the disposal of the infusion set that matches the infusion information stored in the memory after the infusion set information verification operation.

Figure 10:
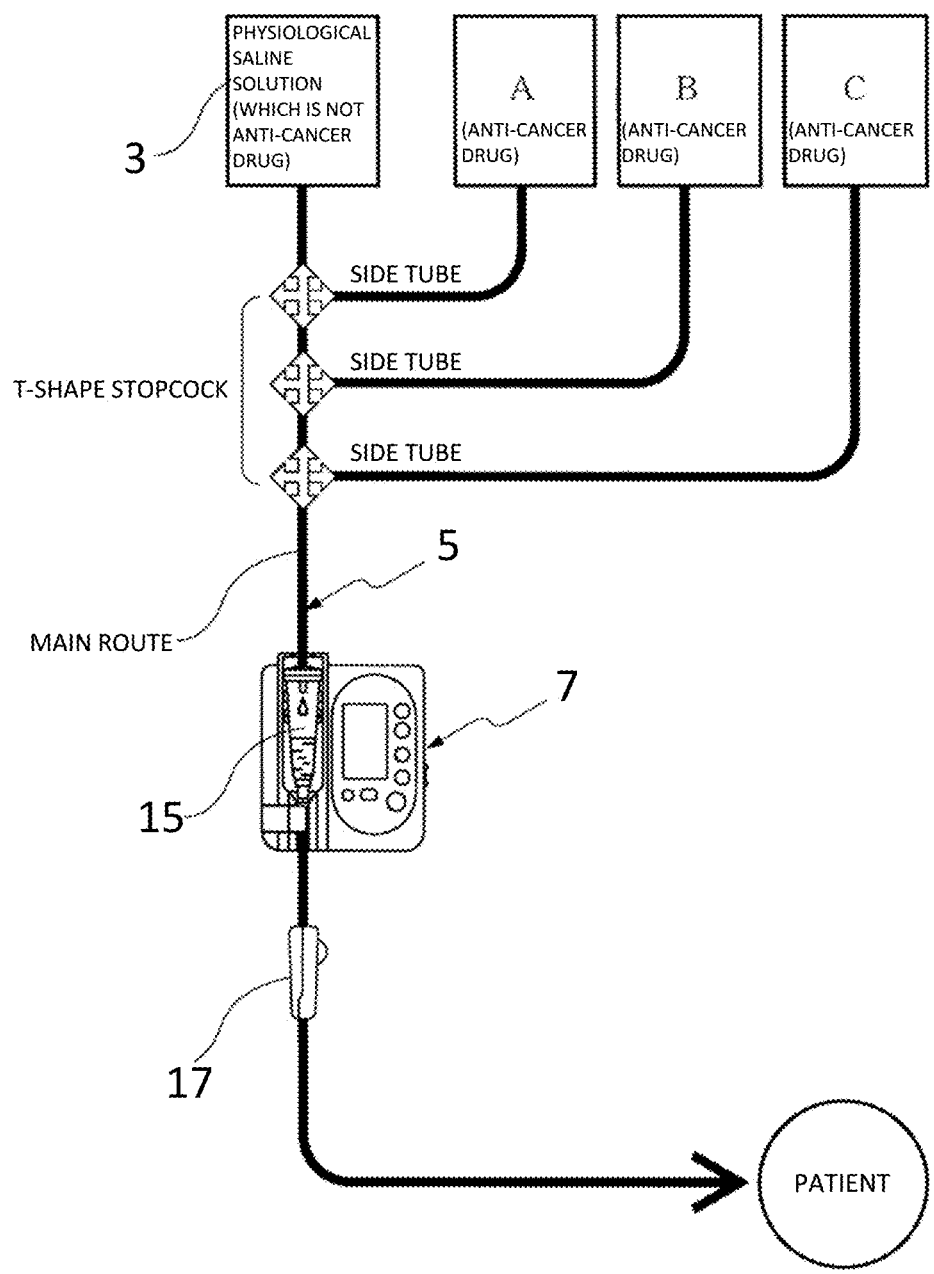

FIG. 10 is a configuration diagram showing an infusion line in a case in which anti-cancer drugs are sequentially infused by means of the automatic infusion device of the infusion injection system shown in FIG. 1.

Figure 11:
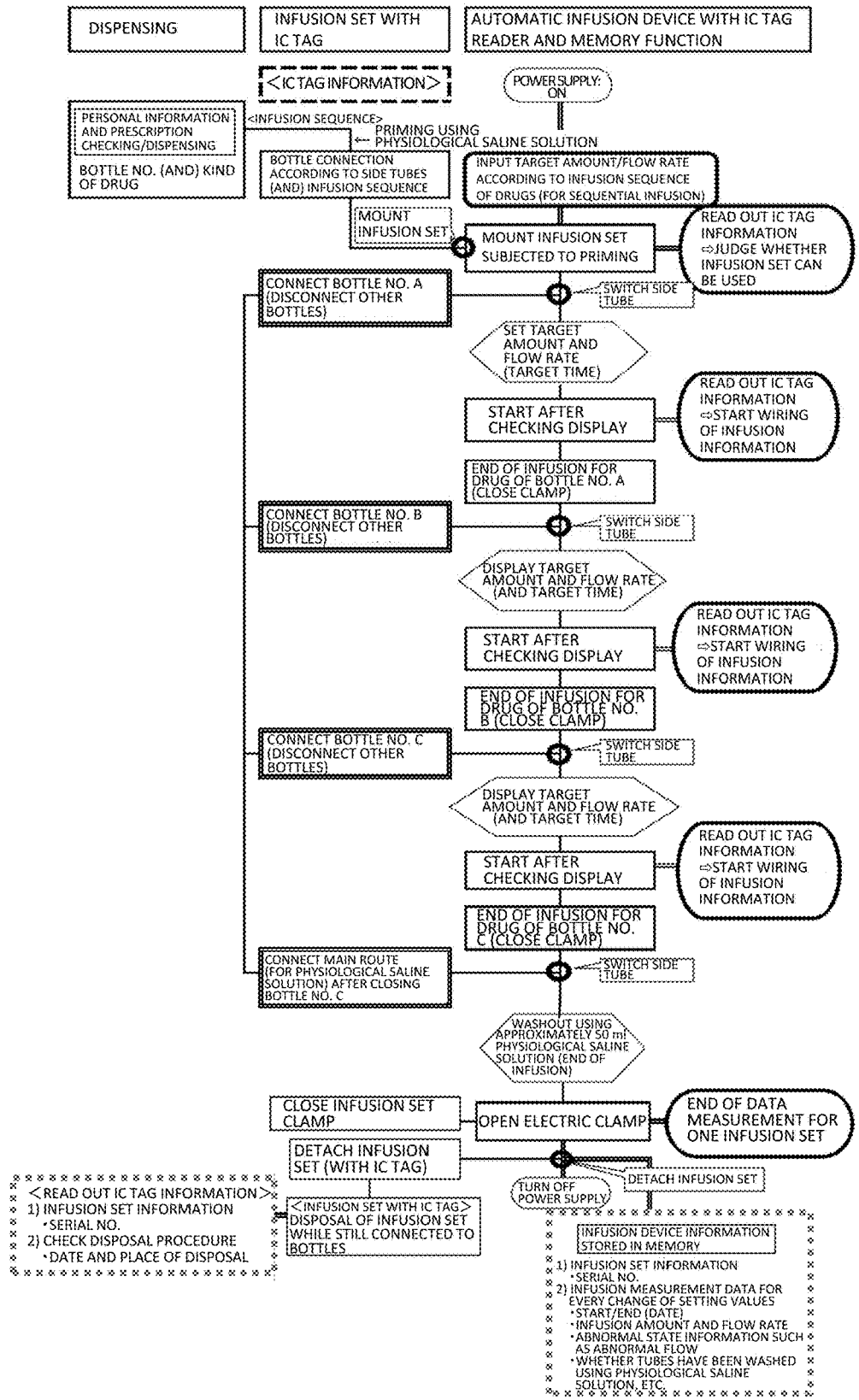

FIG. 11 is a diagram showing an overall operation flow in a case shown in FIG. 10.

Figure 12:
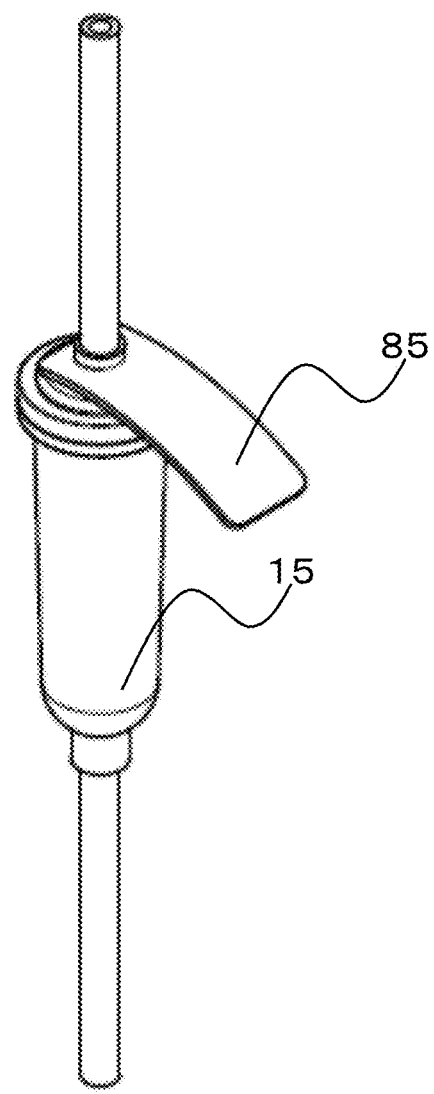

FIG. 12 is a diagram showing another example of the IC tag.

DESCRIPTION OF EMBODIMENTS

Detailed description will be made below with reference to the drawings regarding embodiments of the present invention. However, the present invention is by no means restricted to such arrangements.

FIG. 1 is an overall view showing a state in which an infusion injection system according to an embodiment of the present invention is employed. Description will be made below regarding a natural-fall infusion injection system 1. The infusion injection system 1 includes an infusion set 5 to be connected to an infusion bottle 3 and an automatic infusion device 7. The infusion bottle 3 is hung from the top of an infusion stand 9. The automatic infusion device 7 is mounted on the infusion stand 9 via a mounting arm 10. The infusion set 5 includes an introduction needle 11 to be connected to the infusion bottle 3, a drip tube 15 connected to the introduction needle 11 via a tube 13a, a manual clamp 17 connected to the drip tube 15 via a tube 13b, and an infusion needle 19 connected to the manual clamp 17 via a tube 13c. The manual clamp 17 is configured to regulate the flow provided by the infusion set 5. The infusion needle 19 is to be inserted into an arm or the like patient.

Figure 2:
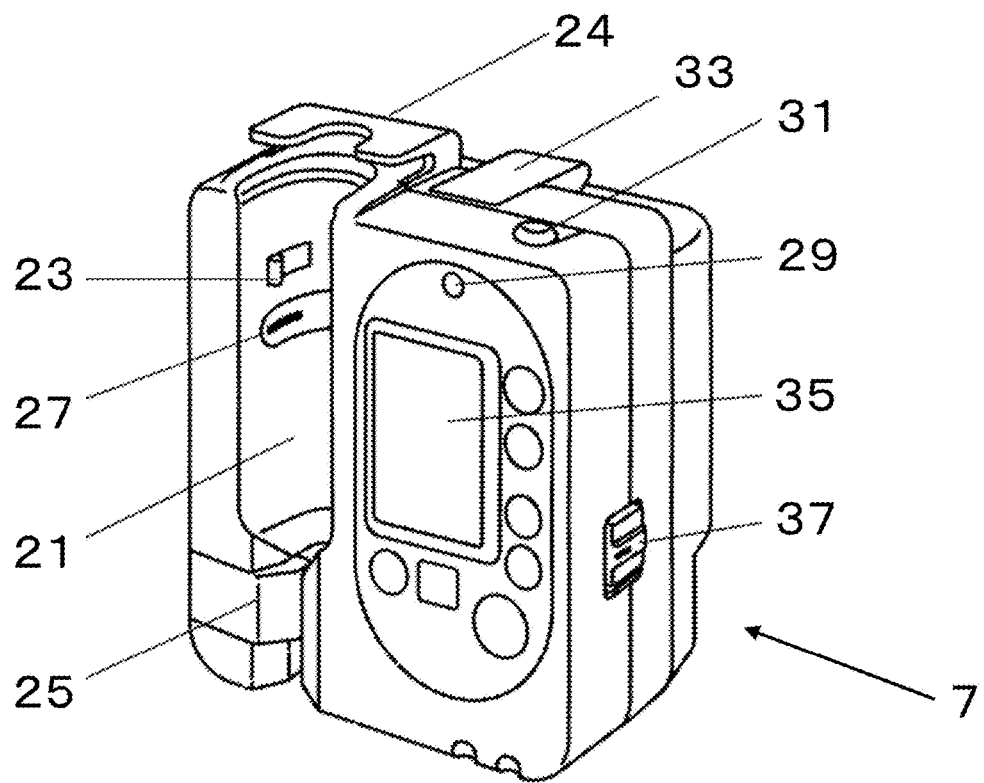
FIG. 2 is a perspective view showing a main body of an automatic transfusion apparatus of the transfusion system shown in FIG. 1.
Figure 4:
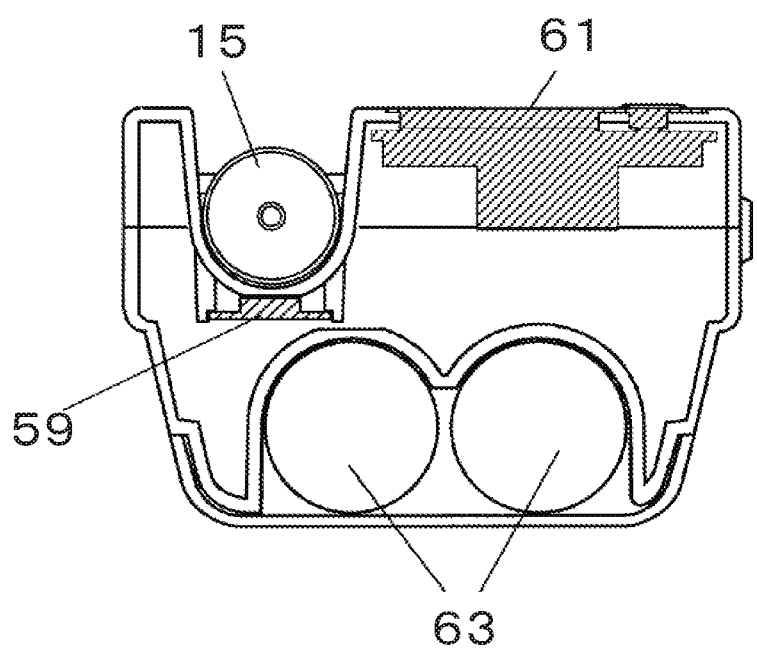
FIG. 4 is a schematic diagram taken along the line S-S in FIG. 3, showing a state in which an IC reader is mounted on the main body of the automatic infusion device such that it is adjacent to an IC tag of a mounted drip tube.
Figure 5:
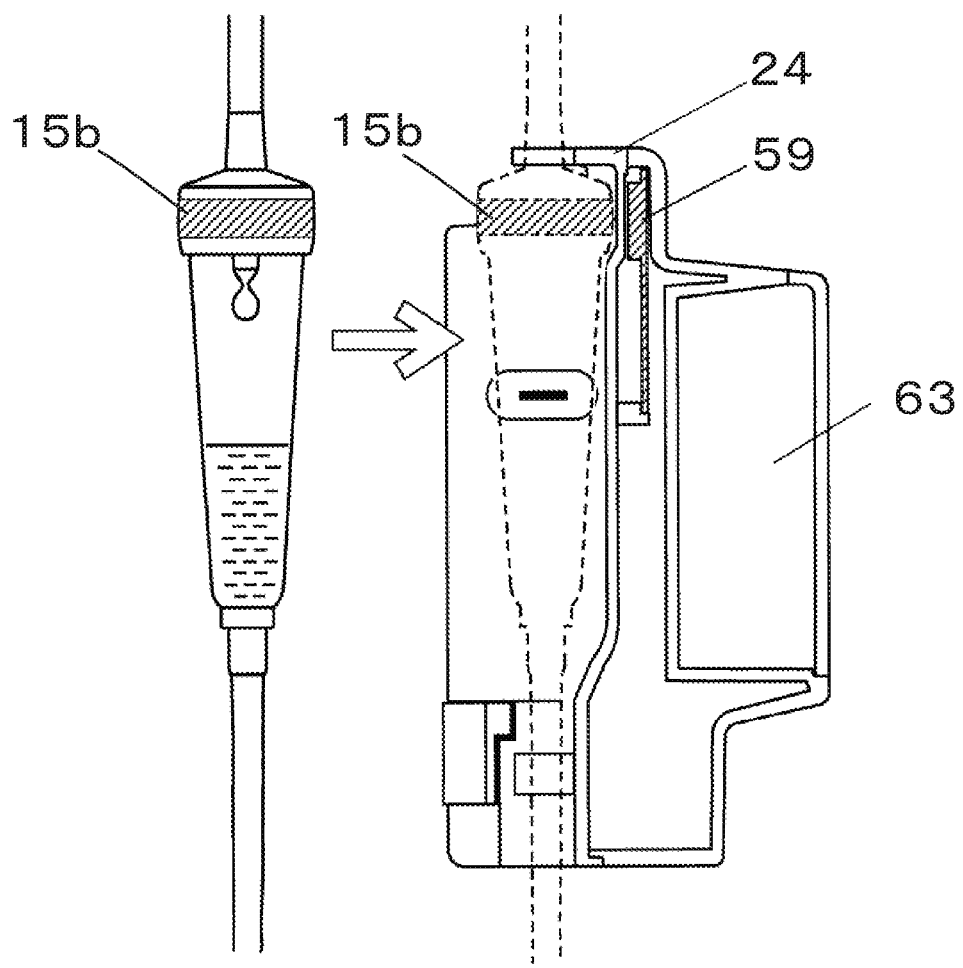
FIG. 5 is a side view for describing a state in which the drip tube is mounted, which is shown as a front view in FIG. 3.

FIG. 2 is a perspective view of a main body of the automatic infusion device 7 of the infusion injection system 1 shown in FIG. 1. FIG. 3 is a front view showing a state in which a drip tube including an IC tag is mounted on the main body of the automatic infusion device of the infusion injection system shown in FIG. 1. As shown in FIGS. 2 and 3, in this example, the drip tube 15 is mounted such that it is surrounded by the main body of the automatic infusion device on three sides. FIG. 4 is a schematic cross-sectional view taken along line S-S in FIG. 3. As shown in this drawing, an IC reader is arranged on the main body of the automatic infusion device such that it is adjacent to the IC tag of the drip tube thus mounted. FIG. 5 is a side view for describing a state in which the drip tube is mounted, which is shown as a front view in FIG. 3. FIGS. 6A and &B are diagrams for describing the IC tag mounted on the drip tube shown in FIG. 3. Specifically, FIG. 6A is a front view showing the drip tube having a cap portion to which a sheet-shaped IC tag is fixedly adhered. FIG. 6B is a back view showing the sheet-shaped IC tag as viewed from the adhered face thereof, and showing a layout thereof including an antenna and an IC chip The automatic infusion device 7 is provided with a drip tube mounting unit 21 on which the drip tube 15 is to be mounted. The drip tube mounting unit 21 is provided with a drip tube holder 23. Furthermore, a drip tube hanger 24 is provided to an upper portion of the automatic infusion device 7. Moreover, a tube door 25 is provided to a lower portion of the drip tube mounting unit 21. The tube door 25 is configured to perform positioning of the tube 13b and to hold the tube 13b. Furthermore, the tube door 25 has a function of ensuring correct mounting of the drip tube 15 connected to the tube 13b with appropriate positioning, in addition to the aforementioned function of positioning of the tube 13b. That is to say, in a state in which the drip tube 15 is mounted on the drip tube mounting unit 21, the upper portion of the drip tube 15 is properly held by the drip tube holder 23. Furthermore, such an arrangement allows judgment to be clearly made based on the state of the tube door 25 provided to the lower portion side whether or not the drip tube 15 has been mounted at a normal position. With such an arrangement, a signal indicating that the tube door 25 closed properly, which is used as a signal indicating that the drip tube 15 has been properly mounted on the drip tube mounting unit 21 with appropriate positioning, is transmitted to a control circuit 65 described later with reference to FIG. 6.

Furthermore, the automatic infusion device 7 is provided with a drip sensor 27 that detects a drop of a drug solution that falls through the drip tube 15. Furthermore, the automatic infusion device 7 includes an LED display unit 29, an alarm display unit 31, a fixation hook 33, an LCD display unit 35, a power supply key 37, a liquid amount key 39, a time/flow key 41, an up key 43, a down key 45, a start key 47, a stop/alarm stop key 49, a release key 51, a volume key 53, an infusion set key 55, a flow regulation unit (tube clamp) 57, an IC tag reader unit 59, a substrate 61, and a battery 63.

As shown in the layout relation between the IC tag reader unit 59 and the IC tag 15b in FIGS. 4 and 5, the IC tag reader unit 59 is arranged such that it faces the IC tag 15b in the minimum straight-line distance. This requires only a narrow wireless field to provide data communication. Thus, the sheet-shaped IC tag 15b requires only a very compact IC and a compact antenna having a short antenna length. This allows the IC tag 15b to be mounted on the drip tube 15 even if the drip tube 15 has a narrow space. As shown in FIG. 6A, the sheet-shaped IC tag 15b is adhered to the cap portion 15a on the upper portion of the drip tube 15. By adhering the IC tag 15b to the outer face of the cap portion 15a, this provides a mounting method that is suitable for mass production. It should be noted that the drip tube 15 is provided with a drug solution outlet 15c and a transparent portion 15d positioned below the cap portion 15a. The transparent portion 15d allows the user to monitor a drop falling from the drug solution outlet 15c. The falling drop is detected by the drip sensor 27.

The LED display unit 29, the alarm display unit 31, and the LCD display unit 35 display information as necessary. The liquid amount key 39, the time/flow key 41, the up key 43, the down key 45, the start key 47, the stop/alarm stop key 49, the release key 51, the volume key 53, and the infusion set key 55 are to be operated in order to set the conditions or the like for the infusion on the automatic infusion device 7 side. The setting conditions should match the conditions held by the IC tag 15b, and are set before the automatic infusion device 7 operates. The flow regulation unit (tube clamp) 57 is configured to regulate the flow provided by the tube 13b. The control circuit (mechanism) 65 shown in FIG. 7 is formed on the substrate 61. The battery 63 allows the automatic infusion device 7 to be used as a mobile device, unlike an arrangement employing a wired mechanism.

FIG. 7 is a block diagram showing a control circuit of the automatic infusion device of the infusion injection system shown in FIG. 1 and a configuration relating to the control circuit.

The control circuit (mechanism) 65 is connected to the drip sensor 27. The drip sensor 27 is provided with a light-emitting unit 27a and a light-receiving unit 27b. A drug solution drop falling through the gap between the light-emitting unit 27a and the light-receiving unit 27b is detected. The detection signal is input to the control circuit (mechanism) 65. The IC tag reader unit 59 configured to read out the data stored in the IC tag 15b is connected to the control circuit 65. The data stored in the IC tag 15b is input to the control circuit. (mechanism) 65. The input operation is performed in response to judgment that the drip tube 15 has been mounted on the main body of the automatic infusion device 7 in a proper state. The judgment regarding whether or not the mounting has been properly performed based on judgment regarding whether or not the tube door 25 described above has been closed properly. With the input of this mounting check signal to the control circuit. (mechanism) 65, the IC tag reader unit 59 is configured to perform a readout operation.

The control circuit. (mechanism) 65 is connected to an input mechanism 67, a display mechanism 69, a calculation mechanism 71, a timer mechanism 73, a sound source mechanism 75, and memory 77. These mechanisms are required to perform information processing such as inputting of information such as the date and place of manufacture of the infusion set, the positions and number of side tubes, the material of the infusion set, the kind of bottle needle, and the drip rate of the drip tube (drops/ml). Furthermore, the control circuit (mechanism) 65 is connected to a driver 81 that drives an actuator 79. The control circuit (mechanism) 65 instructs the actuator 79 to drive the flow regulation unit (tube clamp) 57 so as to regulate the flow. A power supply unit 83 including a step-up converter 83a allows the control circuit (mechanism) 65 and the like to operate. In the actual infusion operation, the memory 77 may store at least one information piece from among the infusion start time and date, the total amount of infusion, the flow rate, the occurrence of abnormal flow, and the time at which abnormal flow has occurred the control circuit 65 may be configured to transmit, by means of an unshown transmission mechanism via wireless communication, at least one information piece from among the information about the infusion executed means of the infusion set, i.e., the infusion start time and date, the total amount of infusion, the flow rate, the occurrence of abnormal flow, and the time at which abnormal flow has occurred.

FIG. 8 is a flowchart showing the operation of the automatic infusion device of the infusion injection system shown in FIG. 1. Description will be made below regarding the operation thereof. FIG. 9 is a flowchart showing a procedure including the details of the processing in step 6 shown in FIG. 8, and a procedure from the judgment operation regarding whether or not the infusion set has been normally mounted using the automatic infusion device of the infusion injection system shown in FIG. 1 up to the disposal procedure for disposing of the infusion set that matches the infusion information stored in the memory after the infusion set information verification operation.

In step 1, the settings are made for the infusion set. These settings of the infusion set are made by operating the infusion set key 55 or the like shown in FIG. 3. In step 2, the target infusion amount is input. Upon operating the liquid amount key 39 or the like shown in FIG. 3, this input is performed by the input mechanism 67 shown in FIG. 7. In step 3, the flow rate per hour is input. Upon operating the time/flow key or the like shown in FIG. 3, this input is performed by the input mechanism 67 shown in FIG. 7. In step 4, calculation is performed for the flow rate per unit of time. This calculation is performed by the calculation mechanism 71 shown in FIG. 7. In step 5, the falling drop interval is determined. In step 6, the infusion set information is stored, following which the operations which are to be performed after the infusion set is mounted are executed. Specifically, the operations shown in FIG. 9 are performed.

Referring to FIG. 9, in step 61, storage of the infusion information is started. In step 62, judgment is made regarding whether or not the infusion set has been mounted normally. This judgment is made based on the judgment regarding whether or not the tube door 25 has been closed properly as described above. After the infusion set has been mounted normally, a time count is performed from this time point, which is also recorded. In step 63, infusion set information including a serial number is acquired. Such a serial number is employed in a case in which it is associated with the information with respect to the date and place of manufacture of the infusion set, the positions and number of side tubes, the material of the infusion set, the kind of bottle needle, and the drip rate of the drip tube (drops/ml). Such information is acquired by means of the IC tag reader unit 59 by reading out the data from the IC tag 15b. Subsequently, in step 64, judgment is made regarding whether the infusion set information indicates 20 drops/ml or 60drops/ml. Furthermore, judgment is made regarding whether or not the infusion set information thus read out matches the information set for the automatic infusion device 7.

When the result of the verification is a match, the flow proceeds to step 7. In this step, visual checking is performed by a nurse or the like. That is to say, a double-check is performed, by a machine and by a person. Subsequently, when the infusion start button is pressed, the control circuit (mechanism) 65 shown in FIG. 6 controls the driver 81 so as to drive the actuator 79. As a result, the operations in step 8 and the subsequent steps are performed. In these operations, the flow regulation unit 57 performs an opening/closing operation, and infusion of a drug solution is performed based on the infusion information. It should be noted that, as described above, the drip tube hanger 24 is provided to the upper portion. Furthermore, the tube door 25 is provided. Judgement is made, based on whether or not the tube door 25 has been closed, regarding whether or not the proper mounting state has been obtained when the drip tube 15 is mounted. In some cases, some kind of force can lead to deviation of the orientation of the drip tube 15 or the like, resulting in an inappropriate mounting state. In order to handle such a problem, when the start key is pressed, a photosensor (infrared sensor) employed as a second detection mechanism for detecting the mounting state may operate so as to detect whether or not a proper mounting state has been obtained. After a proper mounting state is confirmed and confirmation has been made that the result of the verification is a match, the infusion of the drug solution may preferably be started based on the infusion information, which provides further improved safety and the like. On the other hand, if the result of the verification is a mismatch, the infusion start button is configured such that the user cannot press the button. Otherwise, in this state, even if the user presses the infusion start button, the infusion of the drug solution is not started based on the infusion information. In this case, the operation in step 7 and the subsequent operations are not executed before the infusion information matches the information set for the infusion device. The control operation for suspending the start of the infusion of the drug solution based on the infusion information is performed as follows. That is to say, the control circuit (mechanism) 65 shown in FIG. 7 does not operate the driver 81 if the result of the verification is a mismatch. As a result of suspension of the driving operation of the actuator 79, the flow regulation unit (tube clamp) 57 does not operate. In this case, an alarm or the like may preferably be issued. Similarly, when judgement is made based on the detection result provided by the second detection mechanism that the drip tube 15 has not been properly mounted, an alarm or the like may preferably be issued.

Returning to FIG. 8, in step 8, the tube clamp 57 is closed. In step 9, the manual clamp 17 is opened. In step 10, the tube clamp 57 is opened. In step 11, falling drop detection is performed. The falling drop detection in step 11 is performed by means of the drip sensor 27 shown in FIG. 7. In step 12, judgement is made regarding whether or not the flow rate matches the setting flow rate with a margin of error of ±10%. When judgment is made that the flow rate does not match the setting flow rate with a margin of error of ±10%, the operation flow proceeds to step 13. In this step, an infusion line normalizing operation is performed, or the user raises or lowers the position of the infusion bag, so as to provide a flow rate that matches the setting flow rate with a margin of error of ±10%. Such operations are performed as a loop operation. When judgment is made that the flow rate matches the setting flow rate with a margin of error of ±10%, as shown in step 14, the infusion operation is continued. With such an arrangement, when the flow rate does not match the setting flow rate with a margin of error of ±10%, judgment may be made that the occurrence of an abnormal state has been detected, and suspension of the control operation may automatically be performed. Otherwise, in this case, the nurse or the like may be notified of the detection of such an abnormal state in the form of an alarm, and the nurse may forcibly suspend the control operation.

When such an abnormal state has occurred, such an arrangement allows the nurse or the like to change the settings. Such a change in the settings becomes acceptable after confirmation has been made that the result of the verification is a match. After the settings have been changed, judgment is made based on whether or not confirmation has been made at least once that the result of the verification is a match. This allows judgment to be made regarding whether the change in the settings is due to human error or otherwise due to a flexible response according to human judgment based on the situation of the medical treatment site. This provides a system that supports flexible responses according to the situation of the medical treatment site while suppressing human error. As a result, this allows the infusion to be performed for the patient with the conditions changed as a result of a flexible response according to human judgment with reference to judgment by the machine. It should be noted that, once confirmation has been made that the result of the verification is a match, the settings may be changed even before an abnormal state occurs, e.g., even before the nurse presses the start button. This provides a system that supports a flexible response according to human judgment with reference to judgment of the machine regardless of the occurrence of an abnormal state. After the infusion operation ends via such steps, disposal of the infusion set is performed.

It should be noted that, as shown in FIG. 9, in step 7, at the same time as the infusion start button is pressed, the infusion information is stored (infusion start time, target amount, flow rate, history of alarms such as a flow abnormal state alarm and the like, and time points at which an abnormal state has occurred, flow suspension history, time points at which the flow is suspended, changes in the target infusion amount, time points at which the target infusion amount has been changed, changes in the setting value of the flow rate, time points at which the setting value of the flow rate has been changed, infusion end time, infusion set detaching time, and the like).

FIG. 10 is a configuration diagram showing an infusion line that supports sequential anti-cancer drug infusion using the automatic infusion device of the infusion injection system shown in FIG. 1. In this example, in order to support the infusion of multiple bottles of anti-cancer drugs by means of a single infusion set (drip tube), side tubes and T-shape stopcocks, the number of each of which matches the number of bottles of anti-cancer drugs used in the infusion, are arranged between the infusion bottles 3 and the drip tube 15.

Before the infusion is started, priming is completed, i.e., the infusion line of the infusion set 5 is filled with a physiological saline solution. Subsequently, the bottles of anti-cancer drugs are sequentially infused according to a doctor's instructions. Specifically, when the infusion of an ant-dancer drug A ends, the infusion is temporarily suspended. After the target infusion amount and the target flow rate are set for an anti-cancer drug B, the infusion is restarted. In the same way, when the infusion of the anti-cancer drug B ends, the infusion is suspended. After the target infusion amount and the target flow rate are set for an anti-cancer drug C, the infusion is restarted again. When the infusion amount reaches the target infusion amount, the infusion is stopped. In this stage, the infusion has been completed for the anti-cancer drugs A, B, and C.

In this state, a highly toxic anti-cancer drug remains in the main route of the infusion set 5. Accordingly, disposal of the infusion set 5 cannot be performed in this state. In order to solve such a problem, after washout is performed using predetermined amount of physiological saline solution, which is not an anti-cancer drug, disposal of the infusion set 5 is performed. Typically, each introduction needle communicating with a bottle of an anti-cancer drug is left in a state in which it is inserted into an infusion bottle 3, and disposal is performed in this state after the infusion set 5 is put into a dedicated bag. If an introduction needle 11 inserted into an infusion bottle 3 is detached from the infusion bottle 3 of the anti-cancer drug, only a small amount of the anti-cancer drug is exposed to the air, which can become a risk of "anti-cancer drug exposure", and it is regarded as being necessary to avoid this risk.

From the following viewpoints, the system shown in FIG. 1 and the like is effectively applicable to a case of employing the infusion bottles 3 and multiple kinds of anti-cancer drugs A, B, and C.

FIG. 11 is a diagram for describing the operation of the system shown in FIG. 1 and the like in the case of employing the multiple kinds of anti-cancer drugs A, B, and C, as shown in FIG. 10. Detailed description will be made regarding the matters described above.

The overall flow shows a procedure from a step in which the target amount and the target flow rate are input beforehand for each of the anti-cancer drugs A, B, and C, up to an infusion set disposal step. In this case, sequential infusion is performed using multiple kinds of drugs by means of a single infusion set. Specifically, an infusion sequence is sequentially performed. Such a sequential anti-cancer drug infusion is performed for a single patient. In the first step, priming is performed with a physiological saline solution. In the second step, the anti-cancer drug A is infused. In the third step, the anti-cancer drug B is infused. In the fourth step, the anti-cancer drug C is infused. In the fifth step, washout with a physiological saline solution is performed. The information with respect to the kinds of anti-cancer drugs, i.e., the kinds of the anti-cancer drugs A, B, and C, the amount to be infused (target amount) and the infusion rate (flow rate), which have been determined based on the patient's symptoms, changes in the patient after administration of the drug solution, the physical size of the patient, the age of the patient, the patient's medical history, and the like, are carefully input by the nurse or the like to the infusion device according to the instructions of a doctor.

Here, redundant description will be made for confirmation regarding the infusion information stored in at least the automatic infusion device and the information written to at least the IC tag. First, the infusion information stored in at least the automatic infusion device is configured according to a temporal axis, and includes setting values, the start/end of infusion, changes in the target amount and changes in the flow rate, the occurrence of abnormal state such as an abnormal flow, the start/end of tube washout using a physiological saline solution, etc. On the other hand, the information written to at least the IC tag is stored such that it is associated with a serial number or the like. This information includes manufacturer information, the sterilization expiration date, the expiration date for use, the storage standards, product specifications (number and positions of side tubes, size, material, drip size (drops/mL), etc.), identification number, and the like.

Description will be made below as appropriate with reference to FIG. 11.

First, a nurse or the like executes priming with a physiological saline solution, which secures an infusion line. Anti-cancer drugs are highly toxic. If the priming is executed with such an anti-cancer drug, there is a high potential to involve damage to the human body due to leakage of the anti-cancer drug in the priming. Accordingly, the priming is designed to make use of a physiological saline solution. Description will be made again for confirmation regarding the priming. The priming is a preparation step in which the infusion tube is filled with a solution to be infused, which allows the infusion tube to be immediately connected to an intravenous needle inserted into a blood vessel.

Next, the nurse or the like turns on the power supply. Furthermore, the nurse or the like accurately mounts an infusion set subjected to the priming on an infusion device after the setting values are input beforehand to the infusion device for infusing three kinds of anti-cancer drugs. After the infusion set is accurately mounted, the infusion device reads out the information stored in the IC tag provided to the infusion set. The infusion device displays information regarding the acceptability of starting the infusion, based on the basic information verification as shown in the following table 1, for example.

TABLE 1

Information for verification of whether or not infusion set can be used

| Items | Content |
|---|---|
| 1) Identification number | C000000000001 |
| 2) Manufacturer information | Address/company name/phone number, etc. |
| 3) Product information | Sterilization expiration date (expiration date for use), storage standards, etc. |
| 4) Product specifications | Number and positions of side tubes, size, material, drip rate (drops/mL), etc. |

After the nurse or the like confirms the "acceptable" display for the start of the infusion, T-shaped stopcocks for the physiological saline solution, the anti-cancer drug B, and the anti-cancer drug C are manually closed, and a line for only the anti-cancer drug A is secured.

The nurse or the like instructs the infusion device to display, on its display unit, the target amount and the target flow rate for the anti-cancer drug A stored as the setting data beforehand. Based on the displayed setting information, the nurse or the like visually confirms whether or not the setting conditions are correct. (see Table 2).

The nurse or the like carefully checks the setting values. When the setting conditions are correct, the nurse or the like presses the start button for starting the infusion (see Table 2). In this stage, the infusion device reads out the information stored in the IC tag provided to the infusion set. Furthermore, judgment is made based on the verification result of the basic information regarding whether or not the start of infusion is acceptable. If the judgment is "acceptable", writing of the infusion information for the anti-cancer drug A is started. (see Table 2).

TABLE 2

Start of writing of infusion information (bottle A)

| 1) Identification number | C000000000001 |
|---|---|
| (a) Setting values | Target amount, flow rate (time), infusion set (drops/mL), remaining battery level, volume |
| (b) Infusion start time | Year 20**, month **, day **, hour **, minute ** |
| (c) Change in target amount and flow rate | ** mL/h, change in flow rate for every predetermined time period: ** |
| (d) Occurrence of abnormal flow and other abnormal states, and time points at which abnormal states have occurred | Abnormal values of item (c), or, time points at which electric or mechanical factors that can cause abnormal flow have occurred and content of abnormal state |

If the judgment is "unacceptable", a corresponding alarm is displayed. Examples of such alarms include an alarm that indicates that a side tube to be used in the sequential infusion has been connected to an incorrect portion, which leads to the potential to infuse a different drug from that planned for infusion.

When the bottle becomes empty after the infused amount of the anti-cancer drug A reaches the target value, the T-shaped stopcock for the anti-cancer drug A is manually closed. Subsequently, the nurse or the like instructs the infusion device to display, on its display unit, the target amount and the flow rate for the anti-cancer drug B to be infused in the next stage. The nurse or the like again checks whether or not the setting values thus displayed are correct. (see Table 3).

Subsequently, infusion of the anti-cancer drugs B and C is sequentially performed in the same manner (see Tables 3 and 4). When the bottle of the anti-cancer drug C becomes empty after the infused amount of the anti-cancer drug C reaches the target value, the nurse or the like manually closes the T-shaped stopcock for the anti-cancer drug C. Furthermore, only the infusion line for physiological saline solution released. In this step, the physiological saline solution remaining after the priming (approximately 50 ml, for example) is used. Upon pressing the start button after the washout flow rate determined in the hospital is set, the infusion device reads out the information stored in the IC tag provided to the infusion set. Furthermore, judgment is made regarding whether or not the start of infusion is acceptable, based on the basic information verification (information that indicates whether or not the sequential infusion has been completed for the bottles A, B, and C, the number of which corresponds to the number of the side tubes). If the judgement is "acceptable", writing of the infusion information is started (see Table 5). That is to say, the infusion using the remaining physiological saline solution (50 ml for example) is performed in order to remove the anti-cancer drug remaining on the tube inner wall of the infusion set, which is referred to as "washout". In this step, the information stored in the IC tag provided to the infusion set is read out and written to the memory unit of the infusion device. Furthermore, writing of the physiological saline solution infusion information (washout information) is started. When the physiological saline solution bag becomes empty, the completion of the washout is recorded. In this stage, the nurse or the like can perform disposal of the infusion set.

TABLE 3

Start of writing of infusion information (bottle B)

| | |
|---|---|
| 1) Identification number | C000000000001 |
| (a) Setting values | Target amount, flow rate (time), infusion set (drops/mL), remaining battery level, volume |
| (b) Infusion start time | Year 20**, month **, day **, hour **, minute ** |
| (c) Change in target amount and flow rate | ** mL/h, change in flow rate for every predetermined time period: ** |
| (d) Occurrence of abnormal flow and other abnormal states, and time points at which abnormal states have occurred | Abnormal values of item (c), or, time points at which electric or mechanical factors that can cause abnormal flow have occurred and content of abnormal state |

TABLE 4

Start of writing of infusion information (bottle C)

| | |
|---|---|
| 1) Identification number | C000000000001 |
| (a) Setting values | Target amount, flow rate (time), infusion set (drops/mL), remaining battery level, volume |
| (b) Infusion start time | Year 20**, month **, day **, hour **, minute ** |
| (c) Change in target amount and flow rate | ** mL/h, change in flow rate for every predetermined time period: ** |
| (d) Occurrence of abnormal flow and other abnormal states, and time points at which abnormal states have occurred | Abnormal values of item (c), or, time points at which electric or mechanical factors that can cause abnormal flow have occurred and content of abnormal state |

TABLE 5

Start of writing of infusion information (washout)

| | |
|---|---|
| 1) Identification number | C000000000001 |
| 4) Product specifications | Number and positions of side tubes, size, material, drip rate (drops/mL), etc. |
| (a) Setting values | Target amount, flow rate (time), infusion set (drops/mL), remaining battery level, volume |
| (b) Infusion start time | Year 20**, month **, day **, hour **, minute ** |
| (c) Change in target amount and flow rate | ** mL/h, change in flow rate for every predetermined time period: ** |
| (d) Occurrence of abnormal flow and other abnormal states, and time points at which abnormal states have occurred | Abnormal values of item (c), or, time points at which electric or mechanical factors that can cause abnormal flow have occurred and content of abnormal state |
| (e) Tube washout start time | Time point at which washout is started after flow rate is set according to number of side tubes |
| (f) Tube washout end time | Year 20**, month **, day **, hour **, minute ** |

As can be understood from the aforementioned description of the operations, in a case in which infusion is sequentially performed for multiple kinds of highly toxic drugs by means of a single infusion set, by associating the infusion information with the infusion set, the IC tag information can be used as important information. Furthermore, the stored information can be used as clinical data with respect to medication information. Also, the stored information can be used to disclose the infusion information or the like. More specifically, the information to be stored in the automatic infusion device main body includes the IC tag information provided to the infusion set and at least the target amounts and the target flow rates set for infusion of the drugs. In addition, the automatic infusion device main body is capable of storing the infusion start time, the monitoring result of the consecutive infusions from the infusion start time point, the change of the flow rate per unit of time in the infusion data, detection results of an abnormal state that occurs in the infusion, the history of setting value checking operations, the history of setting value changing operations, etc., in the infusion procedure. Such information can be effectively used for investigation into the causes of the occurrence of medical accidents, or can be effectively used for accumulating medical data as big data.

Description will be made below regarding summarized points for confirmation. The aforementioned system shown in FIG. 1 or the like also has the remaining problems with respect to disposal as described above. However, the aforementioned system allows the user to accurately check the information about the executed infusion (target infusion amount, flow rate, infusion start time, infusion end time, number of times infusion has been suspended, time points at which infusion has been suspended, number of times various kinds of alarms have been issued, time points at which such alarms have been issued, etc.). This facilitates developing preventive measures for preventing the recurrence of errors in the infusion. Furthermore, highly toxic drug solution can remain in the infusion set after such anti-cancer drugs have been infused. With such an arrangement, the user is able to perform proper disposal after an appropriate operation is performed. The memory information shown in. FIG. 8 may be configured as the infusion information associated with individual serial numbers assigned to the respective infusion sets 5. This allows information matching to be verified between the kind of drug and an appropriate tube material, and between the number of the drugs to be sequentially infused and the number of side tubes provided to the infusion set. In addition, when the number of times the infusion has been executed stored in the medication history reaches (the number of times infusion of drugs has been sequentially performed +1), judgement may be made that washout has been executed. This allows confirmation to be made that disposal of the infusion set 5 is appropriate. As a result, this prevents the nurses from making a setting error for important items of the automatic infusion device, thereby providing a correct infusion. In addition, this allows the infusion information to be stored and checked, which is used to protect the medical staff mainly from a toxic anti-cancer drug in an anti-cancer drug infusion.

FIG. 12 is a diagram showing another example of the IC tag. As shown in FIG. 12, an IC tag 85 having a structure shown in the drawing may be mounted on the drip tube 15.

1 infusion injection system, 3 infusion bottle, 5 infusion set, 7 automatic infusion device, 9 infusion stand, 10 mounting arm, 11 introduction needle, 13a, 13b, 13c tube, 15 drip tube, 15a cap portion, 15b, 85 IC tag, 15c drug solution outlet, 15d transparent portion, 17 manual clamp, 19 infusion needle, 21 drip tube mounting unit, 23 drip tube holder, 24 drip tube hanger, 25 tube door, 27 drip sensor, 27a light-emitting unit, 27b light-receiving unit, 29 LED display unit, 31 alarm display unit, 33 fixation hook, 35 LCD display unit, 37 power supply key, 39 liquid amount key, 41 time/flow key, 43 up key, 45 down key, 47 down key, 49 stop/alarm stop key, 51 release key, 53 volume key, 55 infusion set key, 57 flow regulation unit. (tube clamp), 59 IC tag reader unit, 61 substrate, 63 battery, 65 control circuit (mechanism), 67 input mechanism, 69 display mechanism, 71 calculation mechanism, 73 timer mechanism, 75 sound source mechanism, 77 memory, 79 actuator, 81 driver, 83 power supply unit, 83a step-up converter.

The invention claimed is:

1. An infusion injection system comprising:
a drip tube comprising an IC tag having readable information with respect to an infusion set to be connected to an infusion bottle; and
an automatic infusion device comprising a main body on which the drip tube is to be mounted,
wherein a drug solution stored in the infusion bottle is infused into a patient via the drip tube provided to the infusion set under conditions determined beforehand according to a control operation of the automatic infusion device,
wherein the automatic infusion device comprises:
a readout mechanism that starts readout of the information with respect to the infusion set held by the IC tag in response to proper mounting of the drip tube on the main body;
a storage mechanism that stores information input beforehand, which is to match the information with respect to the infusion set held by the IC tag;
an information verification mechanism that verifies information matching between the information read out by the readout mechanism and the information stored in the storage mechanism; and
a control mechanism that starts an operation, under the conditions determined beforehand, by the automatic infusion device in response to an operation start signal input by a user when the result of the verification obtained by the information verification mechanism is a match.

2. The infusion injection system according to claim 1, wherein, when the result of the verification obtained by the information verification mechanism is a mismatch, the control mechanism does not start the operation under the conditions determined beforehand by the automatic infusion device.

3. The infusion injection system according to claim 1, configured to allow the user to change the information to be matched which is stored in the storage mechanism once the result of the verification obtained by the information verification mechanism is a match,
and wherein, in a case in which the information to be matched has been changed by the user, the control mechanism starts the operation under the conditions thus changed in response to the operation start signal input by the user, even in a case in which the result of the verification obtained by the information verification mechanism is a mismatch after the change by the user.

4. The infusion injection system according to claim 3, configured as a gravity fed infusion injection system, and further comprising a detection mechanism that detects an abnormal state in which the control operation has not been performed under the conditions determined beforehand or otherwise under the conditions thus changed,
and wherein, after the user forcibly suspends the operation or otherwise the operation is automatically suspended according to an abnormal state detected by the detection mechanism, the control circuit disables restarting of the operation even if the operation start signal is input by the user before the user changes the information stored in the storage mechanism after the suspension of the operation.

5. The infusion injection system according to claim 3, in which the storage mechanism records a information change history.

* * * * *